US006538143B1

(12) United States Patent
Pinschmidt, Jr. et al.

(10) Patent No.: US 6,538,143 B1
(45) Date of Patent: Mar. 25, 2003

(54) WET ADHESION MONOMER AND DERIVED COPOLYMERS FOR LATEX PAINTS

(75) Inventors: Robert Krantz Pinschmidt, Jr., Allentown, PA (US); Khalil Yacoub, Allentown, PA (US); Christian Leonard Daniels, Macungie, PA (US); Kien Van Phung, Allentown, PA (US)

(73) Assignee: Air Products Polymers, L.P., Allentown, PA (US)

( * ) Notice: Subject to any disclaimer, the term of this patent is extended or adjusted under 35 U.S.C. 154(b) by 234 days.

(21) Appl. No.: 09/603,449

(22) Filed: Jun. 26, 2000

(51) Int. Cl.[7] .................. C07D 233/38; C08F 126/08
(52) U.S. Cl. ................ 548/322.1; 548/316.7; 526/263
(58) Field of Search ............ 548/316.7, 322.1; 526/263

(56) References Cited

U.S. PATENT DOCUMENTS

| | | | |
|---|---|---|---|
| 3,369,008 A | 2/1968 | Hurwitz | 260/80.72 |
| 4,111,877 A | 9/1978 | Dixon et al. | 260/29.6 R |
| 4,429,095 A | 1/1984 | Sandri et al. | 526/263 |
| 4,632,957 A | 12/1986 | Welsh et al. | 524/548 |
| 5,496,907 A | 3/1996 | Dochniak et al. | 528/73 |
| 5,739,196 A | 4/1998 | Jenkins et al. | 524/460 |

FOREIGN PATENT DOCUMENTS

GB          2086917          5/1982

*Primary Examiner*—Joseph K. McKane
*Assistant Examiner*—Andrea D. Small
(74) *Attorney, Agent, or Firm*—Mary E. Bongiorno; Russell L. Brewer

(57) ABSTRACT

The reaction of unsaturated carbonates such as vinyl ethylene carbonate with N-aminoethylimidazolidone (TAM) under mild conditions generates a mixture of two vinyl and hydroxy functional imidazolidone carbamates which polymerize readily into acrylate or vinyl acetate based emulsion polymers. The polymers show enhanced wet adhesion (wet scrubbability) in latex paints and coatings.

10 Claims, No Drawings

WET ADHESION MONOMER AND DERIVED COPOLYMERS FOR LATEX PAINTS

BACKGROUND OF THE INVENTION

Coatings and paints represent an extremely large market for polymers. Particularly attractive from an application and safety perspective are so-called latex paints which are a water dispersion of polymer particles, usually prepared by emulsion polymerization. Although a significant reduction or elimination of volatile organic solvents is achieved by these products, the surfactants remaining after water evaporation, coupled with the relatively high molecular weight of the polymers, frequently prevent complete coalescence. Among other failure mechanisms, coatings may be composed of incompletely coalesced particles surrounded by surfactant. The latter represent buried hydrophiles running through the final coating which can readily absorb moisture. The result frequently is inadequate water resistance and, especially, poor wet adhesion, i.e., adhesion to a previously painted surface when wet.

A large number of polymerizable monomers have been proposed for enhancing wet adhesion of coatings and paints. Many of these materials are based on a polymerizable group attached to an imidazolidone (ethyleneurea), or another type of urea group. (Meth)acrylate and (meth)acrylamide units often have been employed to provide the polymerizable function for the monomer. Allylic functionality has also been used to provide a polymerizable function.

The following patents illustrate conventional wet adhesion monomers for use in preparing latex emulsions suited for paints:

British Patent 2 086 917 discloses wet adhesion promoters for aqueous film-forming surface coating compositions based upon acrylic functional ethylene ureas. In forming the wet adhesion monomer an ethylene urea or derivative is reacted with a hydroxy acrylate such as hydroxypropyl acrylate in the presence of a base.

U.S. Pat. No. 4,111,877 discloses wet adhesion monomers based on allyl esters of N-alkyl-omega-(alkylene ureido) carbamic acid in forming emulsion polymers suited for use in paints and coating compositions. The starting material for preparing the wet adhesion monomer is 2-aminoethylethyleneurea. It is formed by reacting diethylenetriamine with urea. The resulting ureido compound then is reacted with allyl.chloroformate to produce the allyl carbamate.

U.S. Pat. No. 3,369,008 discloses N-(cyclic ureido-alkyl) crotonamides for use as a wet adhesion monomers in coating and paint compositions. In the preparation of the wet adhesion monomer, a crotonic halide is reacted with an N-aminoalkyl-N,N'-alkylene urea or thiourea.

U.S. Pat. No. 4,632,957 discloses wet adhesion monomers based on ethylenically unsaturated ethylene and propylene ureas and their use in preparing latex coating compositions. The wet adhesion monomers are prepared by reacting a primary amine or primary alcohol with a monoisocyanate having ethylenic unsaturation. Representative primary amines are based upon imidazolidones. Monoisocyanates having ethylenic unsaturation include isocyanato-ethyl methacrylate and isocyanato propyl methacrylate.

U.S. Pat. No. 5,496,907 discloses a new class of wet adhesion monomers containing a ureido group and optionally nitrile functionality. The ureido compound is formed by cyanoethylating an amino alkylethylene urea or an amino alkylene oxyplkylene ethyl urea. Ethylenic unsaturation is imparted by reducing the nitrile and reacting the resulting amine with a monoisocyanate having acrylic functionality such as isocyanatoethyl methacrylate.

U.S. Pat. No. 4,429,095 discloses cyclic alkylene ureas having residual unsaturation for use as wet adhesion promoters in latex paints. In forming the wet adhesion monomers a mono-(alkylene ureido alkyl) urea or a bis-(alkylene ureido alkyl) urea is reacted with an unsaturated glycidyl ether.

U.S. Pat. No. 5,739,196 discloses latex compositions incorporating wet adhesion promoting monomers. Examples include those primarily having acrylic functionality as the polymerizable unit for the wet adhesion promoting moiety. Specifically, N-(2-methacryloxylethyl)ethylene urea, dimethylaminopropyl acrylate, 2-N-morpholinoethyl acrylate are shown.

BRIEF SUMMARY OF THE INVENTION

This invention relates to wet adhesion monomers having unique polymerizable functionality and to polymer emulsion prepared therefrom. The invention also relates to paint formulations incorporating the polymer having the polymerized wet adhesion monomer incorporated therein.

The wet adhesion monomer is formed by reaction of an unsaturated carbonate selected from the group consisting of vinyl ethylene carbonate and methacryloxypropylene carbonate or allyloxypropylene carbonate, with a wet adhesion promoting moiety, typically urea or a cyclic urea. The preferred polymerizable functionality based upon the reaction of vinyl ethylene carbonate coupled with a wet adhesion providing moiety is represented by the following structures:

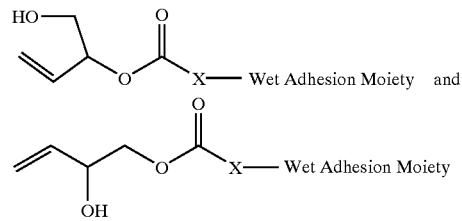

wherein X is NH or O.

The resulting polymers incorporate polymerized units of the wet adhesion monomers and the resulting polymer emulsions are suited for use in producing improved latex paints and coatings.

Advantages of the wet adhesion monomer, the derived polymer emulsions and the latex paints incorporating the polymer emulsions include:

- an ability to synthesize the wet adhesion monomers from readily available starting materials by simple mixing and, most conveniently, in water solution;
- an ability to avoid the use of hazardous solvents, inert atmospheres and long reaction times at elevated temperatures as is common in forming many wet adhesion monomers;
- an ability to use the crude reaction mixture, i.e., a solution of the monomer in water, in a subsequent polymerization without removal of unreacted ethylenically unsaturated starting material, by-products or co-products;
- an ability to use the hydroxy group formed in the carbonate amine reaction as a crosslinking site;
- an ability to react the wet adhesion monomers readily with comonomers, particularly vinyl acetate and acrylate monomers; and, an ability to produce product emulsions that provide good coatings with improved wet adhesion using even small quantities of the wet adhesion monomer.

DETAILED DESCRIPTION OF THE INVENTION

The wet adhesion monomers of this invention are prepared by reacting an unsaturated carbonate with a wet adhesion promoting moiety. terminating in amine or hydroxy functionality, such as a hydroxy or amine terminated alkyl urea or cyclic urea, The unsaturated carbonate typically is vinyl ethylene carbonate (VEC) although methacryloxypropylene or allyloxypropylene carbonate may be used.

Conventionally, ureas and cyclic ureas such as imidazolidones have long been used as wet adhesion moieties for coupling with polymerizable functionality. The five membered cyclic urea, imidazolidone, is most preferred, but urea itself and substituted ureas or larger ring structures can also be used. N-aminoalkyl-N,N'-alkylene ureas or thioureas having a two carbon chain linkage are the two common amine substrates.

Representative structures of possible ureas and cyclic ureas for reaction with the vinyl ethylene carbonate for example are as follows:

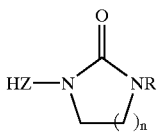

wherein Z is A—$R_0$, wherein A is NH, O and $R_0$ is $C_{1-10}$ alkylene or substituted akylene, and alkylene ether having from 1–6 carbon atoms and n is 1 or 2.

Examples of specific imidazolidones (ethylene ureas) and pyrimidones suited as wet adhesion promoting moieties are as follows:

1-(2-aminoethyl)-2-imidazolidone; 1-(2-aminoethyl)-2-imidazolidinethione; 1-(2-aminopropyl)-4-methyl-imidazolidone; N-methyl-N'-hydroxymethyl ethylene urea, and 1-(3-aminopropyl)-hexahydro-2-pyrimidone. Examples of ureas include N,N'-bis(hydroxymethyl)ethylene urea; N-(2-aminoethyl)urea, 3-aminopropyl urea, and 6-aminohexyl urea.

Other representative wet adhesion promoting urea moieties for synthesis of wet adhesion monomers by reaction with vinyl ethylene carbonate are described in U.S. Pat. Nos. 3,369,008, 4,783,539 and 5,496,907 and are incorporated by reference.

The wet adhesion monomers are preferably prepared at 0 to 100° C., typically 30 to 85° C. in water using near stoichiometric ratios of the polymerizable functional and wet adhesion promoting moieties. Ratios other than stoichiometric, e.g., from 0.5:1 to 1:0.5 are possible. For example, a slight excess of vinyl ethylene carbonate is preferred in order to consume all of the wet adhesion promoting moiety such as N-(2-aminoethyl)ethyleneurea. The reaction can be performed in the absence of solvents or in other solvents as long as at least one reagent is soluble or miscible with the solvent. Polar solvents which can be easily removed after the reaction include water, ethers, lower alcohols, and lower esters.

The emulsion polymers with enhanced wet adhesion can be prepared using polymerizable monomers in ratios commonly used in coatings and paint formulations. Examples of common monomers include lower alcohol ($C_{1-12}$) esters of (meth)acrylic, maleic, fumaric, itaconic, and crotonic acids; styrene; acrylonitrile; vinyl chloride; vinyl acetate and vinyl esters of other linear and branched acids (C1-20); and hydrocarbons such as ethylene; and butadiene. Emulsions based upon $C_{1-8}$ esters of acrylic acid such as methyl acrylate, methyl methacrylate, ethyl acrylate, butyl acrylate, 2-ethylhexyl acrylate are most common. Other monomers include hydroxyalkyl (meth)acrylates, e.g., hydroxyethyl acrylate, hydroxyethyl methacrylate, hydroxypropyl acrylates, hydroxypropyl methacrylate, hydroxybutyl acrylates and hydroxybutyl methacrylates.

Vinyl acetate based emulsions including vinyl acetate/ethylene, vinyl acetate/vinyl decanoate and vinyl acetate/acrylate ester emulsions often are used in paint formulations and these monomers may be polymerized with the wet adhesion monomers. Ethylene is a preferred hydrocarbon comonomer for vinyl acetate polymerization. Also, softening monomers may be incorporated of which many are based upon esters of dicarboxylic acids. Such esters include the reaction products of maleic, fumaric, and itaconic acid and $C_{4-12}$ alcohols. Often dibutyl and dioctyl maleate, etc. are employed as softening monomers.

Functional comonomers at levels of 0.1 to 15% may be included in the emulsion polymer as desired. Examples include (meth)acrylic acid, maleic, fumaric, or itaconic acid and half acid esters, (meth)acrylamides and their derivatives, N-methylolacrylamides, etc., to enhance adhesion to substrates, increase dispersion stability, or provide crosslinking or sites for crosslinking with other post added reagents as are known to those skilled in the art.

The wet adhesion monomers are incorporated into the polymer in amounts of from 0.001 to 10% by weight based upon the weight of total monomers to be polymerized. Preferably, from about 0.1 to 3%, and most preferably at 0.3 to 1% wet adhesion monomers by weight of the total weight of the monomer reactants employed in forming the polymer are employed. Higher levels of wet adhesion monomer can be beneficial when the resulting latex is blended with a wet adhesion monomer free latex in preparing a coating with superior wet adhesion.

Polymers using some combination of (meth)acrylates of $C_{1-8}$ alcohols and vinyl acetate, are chosen for water based paint applications to give glass transition temperatures in the range –25 to +50° C. and preferably from 0 to 45° C.

The emulsion polymerization of the wet adhesion monomer with other monomers is conventional. Typical redox and thermal initiators may be used to initiate the polymerization. Suitable reducing agents or activators include bisulfites and sulfoxylate adducts with aldehydes or acetals, (e.g., sodium formaldehyde sulfoxylate), ascorbic acid or other compounds having reducing properties such as ferrous salts, and tertiary aromatic amines, e.g., N,N-dimethylaniline. Oxidizing agents or initiators include hydrogen peroxide, organic peroxides such as benzoyl peroxide, t-butyl hydroperoxide and the like, persulfates, such as ammonium or potassium persulfate, perborates, and the like. Thermal initiators include azo compounds such as azobisisobutyronitrile or benzoyl peroxide.

The initiator is employed in the amount of 0.01 to 2%, preferably 0.1 to 0.75%, based on the weight of monomers introduced into the system. The activator is ordinarily added as an aqueous solution and the amount of activator, is generally from 0.25 to 1 times the amount of initiator.

A wide variety of emulsifying agents can be used to stabilize the emulsion. Since the reactive monomer is in a neutral form during the copolymerization, no special consideration is needed regarding the compatibility with the stabilizing medium chosen for the reaction.

Suitable non-ionic emulsifying agents for stabilizing the emulsion polymer include polyoxyethylene condensates. Representative polyoxyethylene condensates are represented by the general formula:

R(CH$_2$—CH$_2$—O)$_n$H here R is the residue of a fatty alcohol containing 10–18 carbon atoms, an alkyl phenol, a fatty acid containing 10–18 carbon atoms, and an amide, an amine, or a mercaptan, and where n is an integer of 1 or above.

One class of non-ionic emulsifying agents which can be used include a series of surface active agents known as "Pluronics." The "Pluronics" have the general formula:

$$HO(C_2H_4O)_a(C_3H_6O)_b(C_2H_4O)_cH$$

where a, b, and c are integers of 1 or above. As b increases, the compounds become less water soluble or more oil soluble and thus more hydrophobic when a and c remain substantially constant.

Some examples of non-ionic emulsifying agents sold under the Pluronic trademark which can be used include polyoxyethylene-polyoxypropylene glycols conforming to the above general formula for "Pluronics" in which the polyoxypropylene chain has a molecular weight of 1500 to 1800 and the polyoxyethylene content is from 40 to 50 percent of the total weight of the molecule, a polyoxypropylene having a cloud point of about 140° F. and marketed under the trademark "Pluronic L-64,"; a polyoxyethylene-polyoxypropylene glycol conforming to the above general formula for "Pluronics" in which the polyoxypropylene chain has a molecular weight of 1500 to 1800 and the polyoxyethylene content is from 80 to 90 percent of the total weight of the molecule and having a cloud point of about 212° F. and marketed under the trademark "Pluronic F-68".

Another class of nonionic surfactants are sold under the Igepal trademark. One example within this class is a polyoxyethylene nonylphenyl ether having a cloud point of between 126 and 133° F. and marketed under the trademark "Igepal CO-630"; another is polyoxyethylene nonylphenyl ether having a cloud point above 212° F. and marketed under the trademark "Igepal CO-887." A similar polyoxyethylene nonylphenyl ether with a cloud point of about 86° F. is marketed under the trademark "Igepal CO-610." Surfactants similar to the Igepal surfactants include a polyoxyethylene octylphenyl ether having a cloud point of between. 80° F. and 160° F. marketed under the trademark "Triton X-100", a polyoxyethylene oleyl ether having a cloud point of between 80° F. and 160° F. marketed under the trademark "Atlas G-3915" and a polyoxyethylene lauryl ether having a cloud point above 190° F. marketed under the trademark "Brij 35."

A protective colloid also can be used in the polymerization mixture as a stabilizing agent. Various colloids and amounts conventionally used in emulsion polymerization can be incorporated into the latices as desired and in combination with the surfactants. Representative colloids which can be used include 87–99+% hydrolyzed poly(vinyl alcohol), partially-acetylated poly(vinyl alcohol), e.g., up to 50% acetylated, casein, hydroxyethyl starch, carboxymethylcellulose, gum arabic, and the like.

The amount of emulsifying agents used in emulsion polymerization typically is from 0.5 to 7%, typically 2 to 5% based on the organic phase of the latex regardless of the solids content. The stabilizers employed are, in part, also governed by the use to which the copolymer latex is to be put. By utilizing appropriate levels of surfactant and/or protective colloid, one can obtain latex polymer particles having a variety of average particle size ranges and distributions.

In order to maintain the pH of the system at the desired value, an alkaline buffering agent of any convenient type may be added. Materials known in the art which are compatible with other emulsion compounds can be used as the buffer. The amount of buffer is that sufficient to adjust the pH of the system within the desired range, e.g., 3 to 10 and preferably 3.5 and 8.5. Sodium acetate and sodium carbonate are preferred buffers because of their compatibility with the system and their low cost. The amount of buffer is generally about 0.1 to 0.5% by weight, based on the monomers. Other buffers such as disodium phosphate, and the like, can, however, be used.

The free radical polymerizations are typically done at 50 to 100° C., preferably 70 to 85° C. in batch or delay or continuous fashion using thermal (i.e., AIBN or benzoyl peroxide) or, preferably, redox initiation.

The following examples are provided to illustrate various embodiments of the invention and are not intended to limit the scope thereof.

EXAMPLE 1

Preparation of a Wet Adhesion Monomer from Vinyl Ethylene Carbonate (VEC) and 1-(2-aminoethyl)-2-imidazolidone (TAM)

TAM is conveniently prepared by the elevated temperature reaction of diethylenetriamine with urea, as is well known in the art.

Into a solution of TAM (140.1 g, 0.998 mole, 92 wt. % purity) in water (80 g) was slowly added (dropwise) 142.6 g (1.25 mole) of vinyl ethylene carbonate (VEC). During the addition, the pH dropped from 11.8 to 9.1 and temperature increased from 23 to 54° C. The final product was yellow and viscous at 76 wt. % solids. $^{13}C$ NMR showed two isomers were formed. The product, referred to as WAM in the tables and in the discussion following was an approximately 54/46 mixture of the two possible isomers, plus 20 mole % of unreacted VEC present in excess. There may have been up to 10 mole % of $TAM_2$ urea, a common byproduct in TAM in the reaction product. The reaction chemistry is set forth by the following equations:

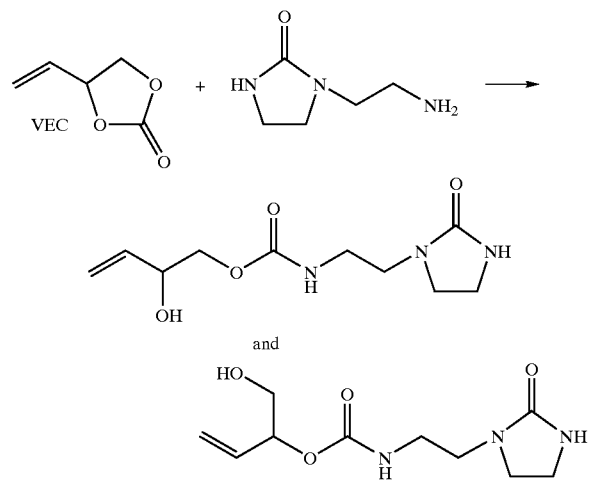

EXAMPLE 2

Effect of a Wet Adhesion Monomer on Emulsion Polymerization

An acrylic ester based polymer of butyl acrylate and methyl methacrylate (50/50 by weight) (BA/MMA) reacted under standard conditions in a bottle reactor gave a reduction in monomer conversion of about 4–5% when 1.8% by weight of the wet adhesion monomer adduct from Example 1 was used. Also there was an increase of coagulum. Using a mixture of vinyl acetate (VAM) and a higher vinyl ester (vinyl decanoate—WV10), gave the following results:

| % by wt of WAM (based on total monomer) | % solid | Sedimentation | coagulum |
|---|---|---|---|
| 0 | 50.0 | 0.5% | trace |
| 0.9 | 48.4 | 0.5% | trace |
| 1.8 | 45.0 | 0.7% | trace |
| 2.7 | 42.7 | 1.0% | visually more |

The data show that the presence of the WAM adduct reduced the rate of conversion as evidence by the lower solids level, but it did not inhibit polymerization. Sedimentation value and coagulum content increased slightly as the percentages of the WAM adduct increased.

EXAMPLE 3

Comparative Polymer Employing a Commercial Wet Adhesion Monomer

One latex which was essentially a commercial product incorporating a wet adhesion monomer based upon the reaction of allyl chloroformate and 1-(2-aminoethyl)-2-imidazolidone sold as WAM IV and the other was based upon a latex incorporating the wet adhesion monomer of Example 1. The level of wet adhesion monomer in each latex was 0.75 wt % on polymer.

| Charges & Feeds | Ingredients | Amount grams |
|---|---|---|
| Initial Charge | DI water | 140 |
| — | Natrosol 250 JR (2%) | 864 |
| | $Na_2S_2O_8$ | 6.9 |
| | Na benzoate | 4.1 |
| | $Fe^{+2}$ ammonium sulfate (5%) | 5.0 |
| Activator Delay | DI water | 477.6 |
| (0.5%) - 163 g added | SFS | 2.4 |
| Catalyst Delay | DI water | 118 |
| 62 g over 180 min, | $Na_2S_2O_8$ | 4.12 |
| | Na benzoate | 1.2 |
| Functional monomer | DI water | 475 |
| 466 g added | VEC/TAM (76%) | 21.67 |
| Monomer Delay | Vinyl acetate | 2041 |
| 2234 g added | Butyl acrylate | 226.8 |
| | Pluronic F-68 | 28.35 |
| | Pluronic L-64 | 9.55 |
| | Igepal CO-887 | 40.5 |
| | Igepal CO-630 | 9.55 |

Pluronic F-68 is a block copolymer of propylene oxide and ethylene oxide having an HLB of 29.0.
Pluronic L-64 is a block copolymer of propylene oxide and ethylene oxide having an HLB of 15.0.
Igepal CO-887 is a nonylphenoxypoly(ethyleneoxy)ethanol having an HLB of 18.7.
Igepal CO-630 is a nonylphenoxypoly(ethyleneoxy)ethanol having an HLB of 17.2.

Procedure:

1. heat to 58° C. with subsurface nitrogen, initial pH 5.6
2. initiate by starting activator solution and monomer at 110 rpm, increase agitation to 250 rpm at 120 min
3. at initiation, start catalyst and functional monomer feeds
4. run monomer delays 4 hr, catalyst 3 hr, activator 4.5 hr
5. free monomer profile 2–3%
6. finish with 2 g of t-butylhydroperoxide in 10 g of DI water The final product was 54% solids with a trace of accelerated sedimentation, viscosity (60 rpm): 394 cp, pH 2.34, grits (100 mesh): 84 ppm, passed mechanical stability test.

EXAMPLE 4

Comparison of Paint Formulations Using Polymer Not Incorporating a Wet Adhesion Monomer and a Wet Adhesion Monomer Containing Polymer A comparison of semi-gloss paints was made using a conventional acrylic based emulsion sold under the trademark Flexbond 325 which did not employ a wet adhesion agent and the emulsion of Example 3. Tables 2 and 3 set forth the formulations and results:

TABLE 2

Standard Semi-Gloss Formulation

| | | | F-325 Control | Ex. 3 WAM F |
|---|---|---|---|---|
| Grind Paste: | Texanol | | 3.50 | 3.50 |
| | Propylene Glycol | | 8.75 | 8.75 |
| | Tamol 731 | | 3.50 | 3.50 |
| | Nopco NXZ | | 0.50 | 0.50 |
| | AMP 95 | | 0.75 | 0.75 |
| | Ti-Pure R-900 | | 62.50 | 62.50 |
| | Kathon LX 1.5% | | 0.25 | 0.25 |
| | Water | | 10.00 | 10.00 |
| | Aerosol O.T. | | 0.38 | 0.38 |
| | Nopco NXZ | | 0.50 | 0.50 |
| | Natrosol 250 MR, 3% | | 43.75 | 43.75 |
| | | Latex % Solids | Control | F |
| Letdown: | Grind Paste (from above) | | 134.4 | 134.4 |
| | Water (17.8 g @ 55%) | | 19.31 | 20.04 |
| | Emulsion (105 g @ 55%) | | | |
| | F325 | 55.8 | 103.49 | |
| | Ex. 3 Emulsion | 56.2 | | 102.76 |

TABLE 3

| | Control | Ex. 3 |
|---|---|---|
| Viscosity: 72 hr. KU | 95.2 | 96.0 |
| 20 Gloss | 18.6 | 12.9 |
| 60° Gloss | 61.6 | 55.0 |
| 85° Sheen | 89.0 | 89.6 |
| Reflectance | 94.8 | 94.8 |
| Contrast Ratio | 0.9768 | 0.9747 |
| Freeze/Thaw | | |
| 60° Gloss vs. Control | | -6.6 |
| Block Resistance (ASTM D4946-89) 3 mil. | | |
| 24 Hr. Dry - 1 Hour R.T. 50% RH | 3.2 | 8.8 |
| 24 Hr. Dry - 6 Hours R.T. 50% RH | 0.0 | 1.3 |
| 24 Hr. Dry - 24 Hours R.T. 50% RH | 0.0 | 1.1 |
| Wet Adhesion | | |
| 4 hr | | |
| 25% Removed | 1 | N/A |
| 50% Removed | 1 | N/A |
| 75% Removed | 1 | N/A |
| 100% Removed | 1 | N/A |
| % Removed @ 1000 Cycles | 100 | 0* |
| 24 hr | | |
| 25% Removed | 1 | N/A |

TABLE 3-continued

|  | Control | Ex. 3 |
|---|---|---|
| 50% Removed | 1 | N/A |
| 75% Removed | 1 | N/A |
| 100% Removed | 1 | N/A |
| % Removed @ 1000 Cycles | 100 | 0 |

*The section next to the F325 was removed, but the remaining area was not removed by the test.

The results show that the VEC/TAM monomer designated WAM when incorporated into the emulsion polymer as in Example 3 and the emulsion incorporated in the paint formulation completely suppressed the removal of coating observed in the control polymer without the wet adhesion monomer.

What is claimed is:

1. In a polymerizable monomer formed by the reaction of an unsaturated moiety with a wet adhesion promoting moiety, the improvement which comprises a polymerizable monomer formed by the reaction of a carbonate selected from the group consisting of vinyl ethylene carbonate, methacryloxypropylene carbonate and allyloxypropylene carbonate and a wet adhesion promoting moiety selected from the group consisting of an alkyl urea and a cyclic urea.

2. The polymerizable monomer of claim 1 wherein the wet adhesion monomer is derived by the reaction of vinyl ethylene carbonate with a wet adhesion moiety and the monomer is represented by the formulas:

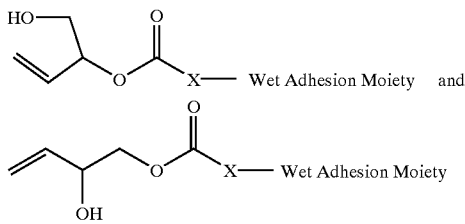

wherein X is NH or O.

3. The polymerizable monomer of claim 2 wherein the wet adhesion moiety is derived from the urea represented by the formula:

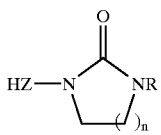

wherein Z is A—$R_0$, wherein A is NH, O and $R_0$ is $C_{1-10}$ alkylene or substituted alkylene, and alkylene ether having from 1–6 carbon atoms, R is H or alkyl having from 1 to 3 carbon atoms and n is 1 or 2.

4. The polymerizable monomer of claim 3 wherein A is NH.

5. The polymerizable monomer of claim 4 wherein n in the formula is 1.

6. The polymerizable monomer of claim 5 wherein $R_0$ is alkylene and has 2 carbon atoms.

7. The polymerizable monomer of claim 1 wherein the wet adhesion promoting moiety is selected from the group consisting of 1-(2-aminoethyl)-2-imidazolidone; 1-(2-aminoethyl)-2-imidazolidinethione; 1-(2-aminopropyl)-4-methyl-imidazolidone; N-methyl-N'-hydroxymethyl ethylene urea, 1-(3-aminopropyl)-hexahydro-2-pyrimidone, N,N'bis(hydroxymethyl)ethylene urea; N-(2-aminoethyl) urea, 3-aminopropyl urea, and 6-aminohexyl urea.

8. The polymerizable monomer of claim 7 wherein the unsaturation is provided by vinyl ethylene carbonate.

9. The polymerizable monomer of claim 8 which is represented by the structures:

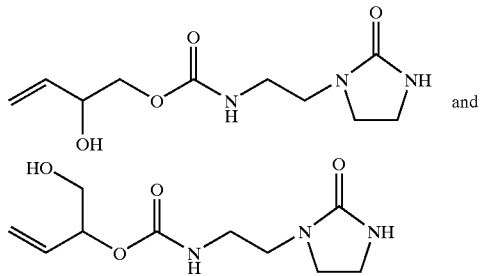

10. The polymerizable monomer of claim 1 wherein the amine is selected from the group consisting of N-(2-aminoethyl)ethyleneurea and the carbonate is vinyl ethylene carbonate.

* * * * *